United States Patent
Grosskopf et al.

(12) 
(10) Patent No.: US 6,506,467 B2
(45) Date of Patent: *Jan. 14, 2003

(54) COMPOSITE HANGER AND LABEL INCORPORATING THE SAME

(75) Inventors: Glenn A. Grosskopf, Lake Zurich, IL (US); Carl W. Treleaven, Greensboro, NC (US)

(73) Assignee: Pharmagraphics (Southeast), L.L.C., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/995,990

(22) Filed: Nov. 28, 2001

(65) Prior Publication Data

US 2002/0056514 A1 May 16, 2002

Related U.S. Application Data (62) Division of application No. 09/384,009, filed on Aug. 26, 1999, now Pat. No. 6,387,202, which is a division of application No. 09/219,589, filed on Dec. 23, 1998, now Pat. No. 6,110,553, which is a continuation of application No. 08/803,945, filed on Feb. 21, 1997, now Pat. No. 5,878,901.

(51) Int. Cl.$^7$ ................................................ B42D 15/00
(52) U.S. Cl. .................. 428/40.1; 40/310; 40/630; 215/399; 248/205.3; 248/683; 283/81; 428/41.3; 428/42.1; 428/42.2
(58) Field of Search .................. 428/40.1, 41.3, 428/42.1, 42.2; 40/310, 630; 215/399; 248/205.3, 683; 283/81

(56) References Cited

U.S. PATENT DOCUMENTS

| | | |
|---|---|---|
| 999,961 A | 8/1911 | Colas |
| 2,135,236 A | 11/1938 | Koppelman .................. 229/90 |
| 2,362,523 A | 11/1944 | Armstrong, Jr. et al. ........ 215/1 |
| 2,635,604 A | 4/1953 | Frederickson ................ 128/272 |
| 3,016,224 A | 1/1962 | Hall ............................ 248/205 |
| 3,231,919 A | 2/1966 | MacDonald .................... 15/174 |
| 3,387,732 A | 6/1968 | Jellies ..................... 215/100 A |
| 3,593,443 A | 7/1971 | Demetrius, Jr. .............. 40/2 R |
| 3,635,367 A | 1/1972 | Morita et al. ........... 215/100 A |

(List continued on next page.)

FOREIGN PATENT DOCUMENTS

| | | | |
|---|---|---|---|
| CH | 408315 | 9/1966 | |
| DE | 2806391 | 8/1978 | ......... B65D/25/22 |
| DE | 3631 021 A | 3/1988 | ......... G09F/3/02 |
| DE | 4321572 A1 | 1/1995 | ......... G09F/3/02 |
| EP | 349670 | 1/1990 | ......... G09I/3/02 |
| EP | 390952 B1 | 6/1994 | ......... G09F/3/02 |
| EP | 356574 B1 | 11/1994 | ......... G09F/3/02 |
| FR | 1460738 | 12/1966 | |
| GB | 1175296 | 12/1969 | ......... A47G/5/00 |
| GB | 1309950 | 3/1973 | ......... F16L/3/02 |

OTHER PUBLICATIONS

Van Leer Flexible Packaging Brochure, *Valeron strength films—Produce samples and technical data*, Copyright 1994 (no month).

*Primary Examiner*—Nasser Ahmad
(74) *Attorney, Agent, or Firm*—Myers Bigel Sibley & Sajovec (57) ABSTRACT

A label for displaying information regarding a container and suspending the container from a support and a method for forming the same. The label includes a base label having a lower surface. A base adhesive is disposed on the lower surface for affixing the label to the container. The label further includes a hanger having at least two interconnected legs defining an opening therebetween, each of the legs having a respective end. Each of the ends of the legs are secured to the base label. The hanger includes at least first and second superimposed layers. The layers are preferably formed of polymeric film. Preferably, the first layer has a tensile strength greater than the second layer and the second layer has a tear resistance greater than the first layer.

22 Claims, 6 Drawing Sheets

U.S. PATENT DOCUMENTS

| | | | |
|---|---|---|---|
| 3,744,658 A | 7/1973 | Fujio | 215/100 A |
| 3,822,492 A | 7/1974 | Crawley | 40/2 |
| 3,851,790 A | 12/1974 | Kasper | 220/85 R |
| 3,884,443 A | 5/1975 | McMaster | 248/467 |
| 3,893,495 A | 7/1975 | Standifer | 150/52 R |
| 3,908,055 A | 9/1975 | Susuki et al. | 428/67 |
| 4,460,143 A | 7/1984 | Ohama | 248/359 |
| 4,462,538 A | 7/1984 | Gendron | 229/68 R |
| 4,479,838 A | 10/1984 | Dunsirn et al. | 156/247 |
| 4,526,404 A | 7/1985 | Vazquez | 283/79 |
| 4,796,937 A | 1/1989 | Andrea | 294/31.2 |
| 4,832,301 A | 5/1989 | Hiramoto et al. | 248/359 H |
| 4,847,130 A | 7/1989 | Cooper | 428/40 |
| 4,948,000 A | 8/1990 | Grabenkort | 215/122 |
| 4,964,512 A | 10/1990 | Ingram et al. | 206/459 |
| 4,964,513 A | 10/1990 | Ingram et al. | 206/459 |
| 4,988,301 A | 1/1991 | Kinberg | 434/410 |
| 5,135,125 A | 8/1992 | Andel et al. | 215/100 A |
| 5,182,152 A | 1/1993 | Ericson | 428/42 |
| 5,227,209 A | 7/1993 | Garland | 428/40 |
| 5,271,642 A | 12/1993 | Jahier et al. | 283/81 |
| 5,284,363 A | 2/1994 | Gartner et al. | 283/81 |
| 5,381,310 A | 1/1995 | Brotz | 362/32 |
| 5,490,658 A * | 2/1996 | Coward | 248/683 |
| 5,542,634 A | 8/1996 | Pomerantz | 248/214 |
| 5,695,466 A | 12/1997 | Lopez et al. | 604/93 |
| 5,695,709 A | 12/1997 | Van Erden et al. | 264/476 |
| 5,738,381 A | 4/1998 | Treleaven et al. | 283/81 |
| 5,782,495 A | 7/1998 | Grosskopf et al. | 281/81 |
| 5,878,901 A * | 3/1999 | Grosskopf | 215/399 |
| 6,015,470 A | 1/2000 | Treleaven et al. | 156/267 |
| 6,110,553 A * | 8/2000 | Grosskopf | 428/40.1 |
| 6,350,502 B1 * | 2/2002 | Grosskopf | 428/40.1 |

* cited by examiner

COMPOSITE HANGER AND LABEL INCORPORATING THE SAME

CLAIM FOR PRIORITY AND CROSS-REFERENCE TO OTHER APPLICATIONS

This application claims priority to and is a divisional of application Ser. No. 09/384,009, filed Aug. 26, 1999, now U.S. Pat. No. 6,387,202 which is a divisional of application Ser. No. 09/219,589, filed Dec. 23, 1998, now U.S. Pat. No. 6,110,553 which is a continuation of application Ser. No. 08/803,945, filed Feb. 21, 1997, now U.S. Pat. No. 5,878,901, issued Mar. 9, 1999, the disclosures of which are hereby incorporated herein by reference in their entireties.

FIELD OF THE INVENTION

The present invention is directed to hangers and labels having hangers for suspending goods or packaging and, more particularly, to hangers having increased strength and tear resistance and to labels including the hangers for identifying and displaying information regarding goods, such hangers and labels providing strong and reliable means for suspending the associated goods or packaging.

BACKGROUND OF THE INVENTION

In administering certain medicines and pharmaceuticals, it is necessary to suspend a bottle or other package containing the pharmaceutical product from a hanger or like support. In particular, intravenously administered fluids are typically contained in a bottle which is suspended from an extended hanger to provide gravity induced flow of the fluid.

It is highly desirable that the container be conveniently and securely suspended. While various separate and detachable harnesses into which the container may be mounted have been used, such harnesses are relatively inconvenient as they require the step of placing the container in the harness or securing the harness about the container in addition to the step of mounting the harness on the hanger. Various other supports have been developed wherein a hanging loop is more or less permanently secured to the container with the hanging loop foldable between an extended position to receive the hanger and a closed position wherein the hanging loop is flat against the bottle. Typically, the hanging loop in the closed position lies adjacent the end of the bottle, often making the container unstable when placed on end. These designs are generally formed of shrink wrapped plastic or foil. As a result, they add considerable additional cost and weight to the overall packaging.

One alternative to the above disclosed hanging and labeling means is disclosed in U.S. Pat. No. 5,135,125 to Andel et al. The Andel reference discloses a label for identifying contents of intravenous feeding bottles having formed as an integral part thereof a hanging ring for suspending the bottle from an intravenous stand. The label is built up from at least one layer of film, a layer of printing ink, and a layer of adhesive. The handle is defined in the label by a pair of die cut lines that penetrate at least the one layer of film in the label. A release coating is applied between the layer of film in the bottle and a portion of the label defined by the handle to permit the handle to be peeled away from the bottle and the remaining portion of the label. As disclosed, the hanger is formed from a single layer of film, preferably polypropylene film.

Another label hanger is disclosed in U.S. Pat. No. 5,490,658 to Coward et al. Hang strips or tabs of the label may be formed of plastic material such as polypropylene, polyethylene, polyester, and so on, or from high strength paper.

One problem commonly experienced with labels such as those disclosed in Andel et al. having film hangers for supporting IV bottles and the like is a tendency for the film of the hanger to tear. The films employed, typically polyester or polypropylene, are strong if there are no tears, nicks, or other imperfections therein and are able to support relatively large loads without requiring an inordinate film thickness. However, if such an imperfection is formed in the hanger or in the hanger attachment points, the properties of the polyester film will cause the imperfection to quickly propagate into a substantial tear when load is placed on the hanger. In practice, it is not uncommon for small cuts or nicks to be formed in the hanger film, particularly along the hanger periphery, during manufacture, handling or when in service. When the damaged hanger is used to support an IV bottle, for example, the small nick or tear becomes a larger tear and often a complete severance of the hanger. As a result, the bottle is allowed to fall from the support. In the hospital environment, such as catastrophic failure of the hanger may in fact be life threatening. The risk of failure is further aggravated in that failure may result from even small, unnoticeable defects in the film.

On the other hand, the IV hanger labels such as those described in Coward et al. using high density polyethylene, there is a tendency for the hanger film to stretch when the IV bottle is suspended therefrom, particularly under heavy loads. This stretching presents a particular problem because the IV bottle may end up too low, thus impeding proper gravity flow of the fluid.

Another problem experienced with hanger labels as described above is that the base portions underlying the hangers must be printed such that the indicia thereon is not covered by the hangers, which are typically opaque. In particular, high density polyethylene is normally opaque and therefore hangers formed of high density polyethylene, for example, as described in Coward et al., will hide any underlying copy. As a result, the layout or copy generally used on the labels must be redesigned to accommodate the hangers. In particular, it may be necessary to relocated a bar code so that it may be read by an electronic scanner.

Thus, there exists a need for a label for identifying and displaying information regarding an article which provides means for suspending the article. There exists a need for such a label which overcomes the drawbacks and deficiencies of the prior art. In particular, there exists a need for such a label which includes a hanger which is strong, stretch resistant, and tear resistant. The hanger should be transparent so that it does not hide indicia on other portions of the label. There exists a need for such a label which may be conveniently and cost effectively manufactured. Further, there exists a need for a method and apparatus for forming such labels.

SUMMARY OF THE INVENTION

Generally, the present invention is directed to a hanger and a label incorporating the same which provides enhanced performance and security as compared with hangers and labels of the prior art. In particular, the hangers provide both improved resistance to tearing and improved resistance to stretching.

The present invention is directed to a label for displaying information regarding a container and suspending the container from a support. The label includes a base label having a lower surface. A base adhesive is disposed on the lower surface for affixing the label to the container. The label further includes a hanger having at least two interconnected legs defining an opening therebetween, each of the legs having a respective end. Each of the ends of the legs is secured to the base label. The hanger includes at least first and second superimposed layers. Preferably, each of the first and second layers and formed by polymeric film. Each of the first and second layers is preferably substantially transparent.

The hanger may be foldable about the ends between a stored position wherein the hanger lies adjacent an upper surface of the base label and a hanging position wherein the hanger is folded away from the base label for receiving the support through the opening.

Preferably, the first layer has a tensile strength greater than the second layer and the second layer has a tear resistance greater than the first layer. The first layer may be formed of polyester and the second layer may be formed of high density polyethylene.

The first and second layers are preferably secured to one another by a layer of hanger adhesive interposed therebetween. Moreover, the first layer, the second layer, and the layer of hanger adhesive are preferably substantially coextensive. The first and second layers may be secured to one another by mechanical adhesion or welding as well.

Photo-luminescent material may be printed one or both of the first and second layers or may be included in an adhesive securing one layers to one another.

The ends of the legs may be secured to an upper surface of the base label by an anchoring adhesive. Further, each of the first and second layers may extend beyond the hanger with the hanger defined by cut lines formed through the first and second layers. At least a portion of at least one of the first and second layers outside of the hanger is secured to the upper surface of the base label by the anchoring adhesive.

In some embodiments, each of the first and second film layers is formed of polyester film.

The hanger may include at least three superimposed polymeric film layers.

The base label may have an upper surface with indicia disposed on the upper surface of the base label. Moreover, at least a portion of the indicia may underlie the hanger when the hanger lies adjacent the upper surface of the base label in a stored position. Preferably, each of the layers of the hanger is formed from a transparent material, whereby the at least a portion of the indicia is visible through the hanger when the hanger is in the stored position.

The present invention is further directed to a method for forming a label for displaying information regarding a container and suspending the container from a support. The method includes providing a first web having an upper surface, a lower surface, and a first adhesive coating the lower surface thereof. A second adhesive is applied to at least one of the upper surface of the first web and a lower surface of a second web, the second web including at least first and second superimposed layers. The second web is married to the first such that a portion of the lower surface of the second web is secured to the upper surface of the first web by the second adhesive. The second web is cut down through each of the first and second layers and to the first web to form a hanger therein. The first web is cut through to form a base label therein.

The method may include the step of removing a second web waste matrix following the step of cutting the second web. Preferably, in such case, the step of cutting the second web to form the hanger includes forming a hanger having at least two spaced apart legs, and the step of removing the second web waste matrix includes removing an interior waste portion forming a part of the second web and defined between the legs of the hanger.

The method may further include the step of applying a third layer of adhesive between the first and second layers of the second web. A first web waste matrix may be removed following the step of cutting the base web. The method may further include the step of printing on the first web. A release varnish may be selectively applied to the upper surface of the first web prior to marrying the second web to the first web.

Each of first and second layers of the second web may be a polymeric film. Preferably, the first layer has a tensile strength greater than the second layer and the second layer has a tear resistance greater than the first layer. Preferably, each of the first and second layers is substantially transparent.

The present invention is further directed to a hanger having at least two interconnected legs defining an opening therebetween. Each of the legs has a respective end. The hanger includes at least first and second superimposed polymeric film layers.

Preferably, in the label as just described, the first layer has a tensile strength greater than the second layer and the second layer has a tear resistance greater than the first layer. The first layer is preferably formed of polyester and the second layer is preferably formed of high density polyethylene. Preferably, each of the first and second layer is substantially transparent.

The first and second layers may be secured to one another by a layer of hanger adhesive interposed therebetween. The first layer, the second layer, and the layer of hanger adhesive are preferably substantially coextensive. The first and second layers may be secured to one another by mechanical adhesion or welding as well.

Photo-luminescent material may be printed on one or both of the first and second layers or may be included in an adhesive securing the layers to one another.

In some embodiments, the hanger includes at least three superimposed polymeric film layers.

In some embodiments, each of the first and second superimposed polymeric film layers are formed of polyester film.

The present invention is further directed to a label for displaying information regarding a container and suspending the container from a support as follows. The label includes a base label having a lower surface. A base adhesive is disposed on the lower surface for affixing the label to the container. A hanger is provided having at least two interconnected legs defining an opening therebetween, each of the legs having a respective end. Each of the ends of the legs is secured to the base label. The hanger includes a scrim and a backing layer secured to the scrim.

The backing layer may be a polymeric film. Preferably, the backing layer and the scrim are each transparent. The backing layer may be secured to the scrim by adhesive. A second backing layer may be secured to the scrim, with the first and second backing layers disposed on opposed surfaces of the scrim. Preferably, the second backing layer is also transparent.

The present invention is further directed to a hanger having at least two interconnected legs defining an opening therebetween. Each of the legs has a respective end. The hanger includes a scrim and a backing layer secured to the scrim. Preferably, the hanger is constructed as described above.

An object of the present invention is to provide a hanger for suspending goods or packaging which is strong, stretch resistant, and tear resistant.

Moreover, an object of the present invention is to provide a label for identifying and displaying information regarding goods contained in a package such as a bottle which includes such a hanger for suspending the associated goods or packaging.

A further object of the present invention is to provide a label as described above which will support relatively large loads without tearing or stretching.

An object of the present invention is to provide such a label and hanger wherein the hanger is substantially transparent so that indicia disposed on the label and underneath the hanger is not hidden from view.

Moreover, an object of the present invention is to provide a hanger and a label as described above which may be conveniently and cost effectively manufactured.

Yet another object of the present invention is to provide a method and apparatus for forming hangers and labels as described above.

The preceding and further objects of the present invention will be appreciated by those of ordinary skill in the art from a reading of the Figures and the detailed description of the preferred embodiment which follow, such description being merely illustrative of the present invention.

DETAILED DESCRIPTION OF THE PREFERRED EMBODIMENTS

Figure 1:
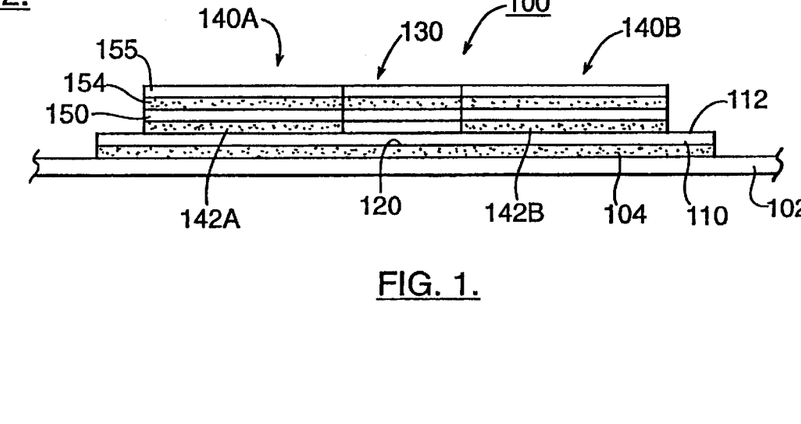
FIG. 1 is a side elevational view of a first embodiment of a label including a composite hanger according to the present invention disposed on a release liner.
Figure 2:
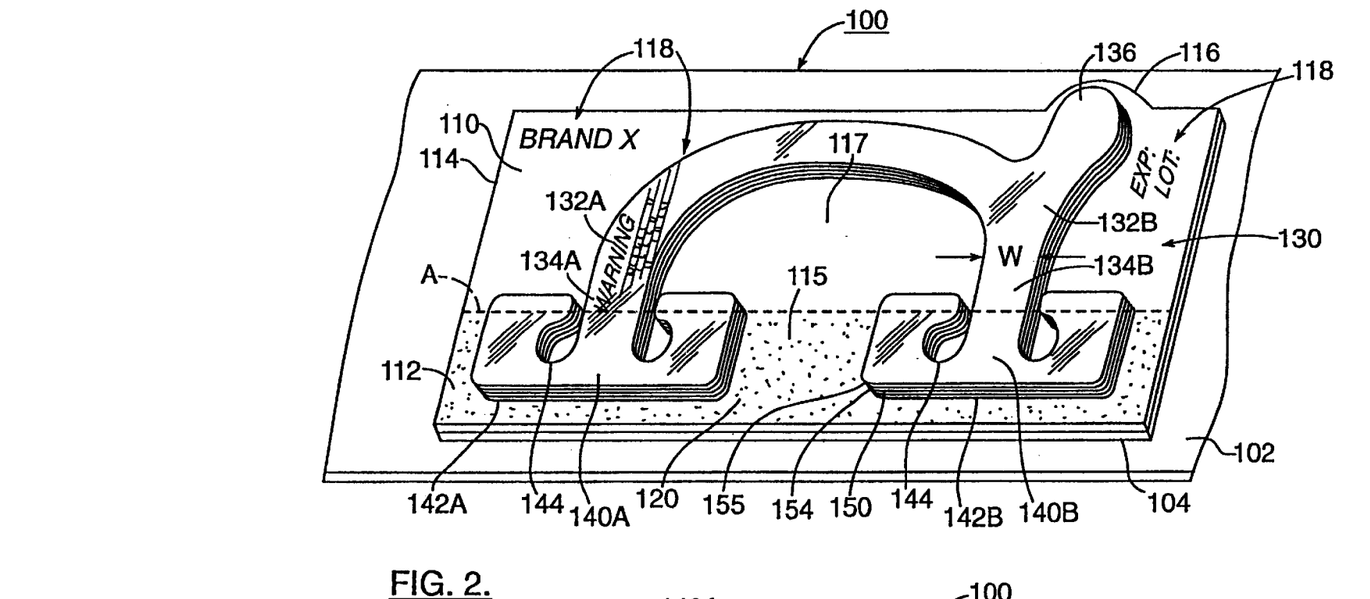
FIG. 2 is a perspective view of the hanging label according to the first embodiment disposed on the release liner.
Figure 3:
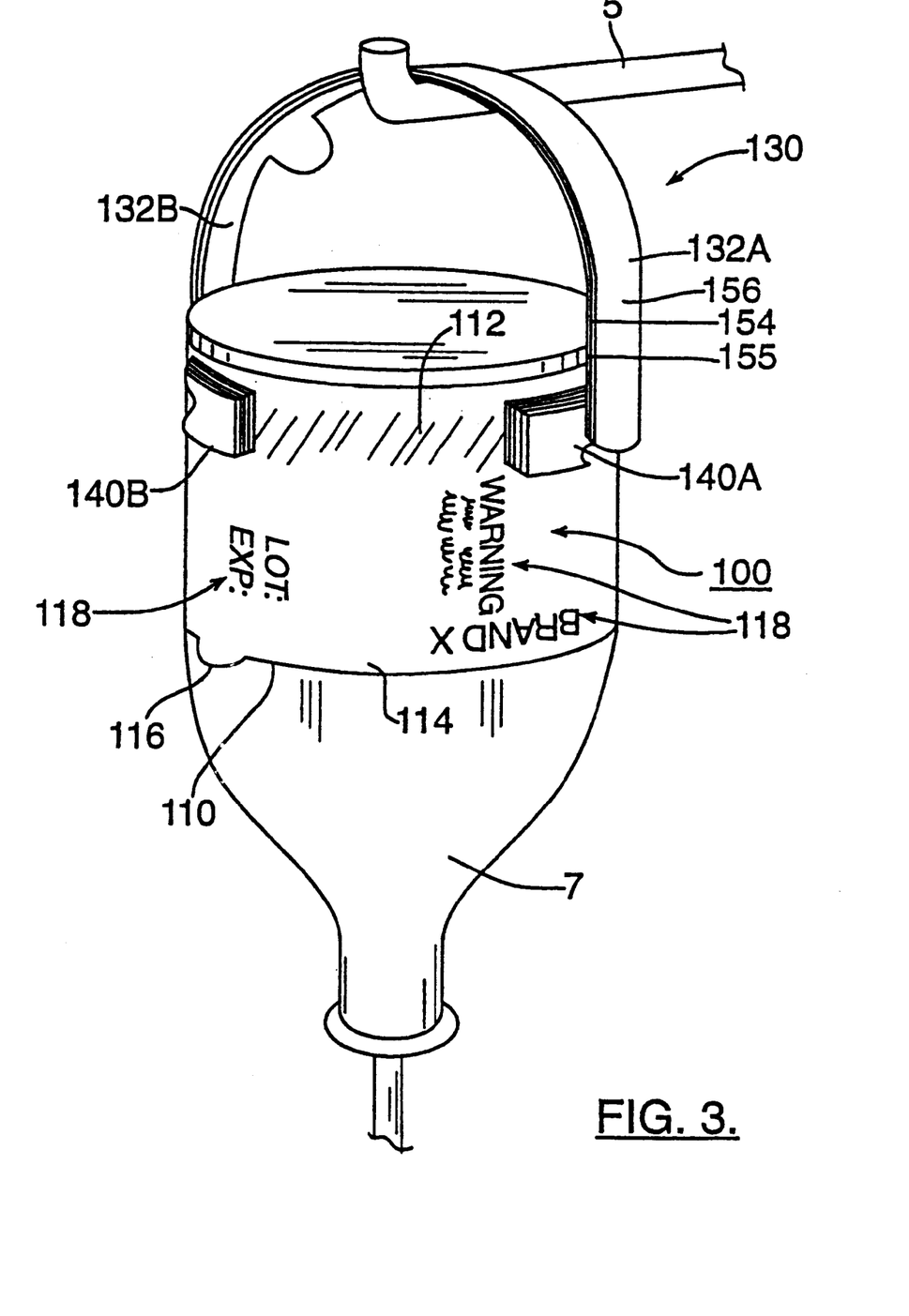
FIG. 3 is a perspective view of the label according to the first embodiment affixed to a container and suspended by the hanger from a support.

With reference to FIGS. 1, 2, and 3 a label 100 according to a first embodiment of the present invention and including a composite hanger 130 is shown therein. Hanger 130 has a multi-ply construction. The materials of the plies are selectively chosen to provide hanger 130 with improved break strength, stretch resistance, and tear resistance. The materials are also selected and processed so that the hanger is substantially transparent. Further, the materials are well suited for use in automatic manufacture of the labels.

As shown in FIGS. 1 and 2, label 100 is releasably secured to a release liner 102 by adhesive 104. Label 100 may be removed from release liner 102 and applied to a suitable container 7 as shown in FIG. 3 by conventional means including, for example, automatic applicator equipment. Once affixed to container 7 means of adhesive 104, label 100 will serve by means of indicia 118 to display information regarding container 7 and its contents. Further, hanger 130 forming a part of label 100 may be folded away from base 110 and container 7 whereupon it may be looped over a suitable support 5 for suspending container 7.

Turning to label 100 in greater detail, base label 110 may be formed from any suitable film or paper stock. Further, base label 110 may be formed from a self adhesive pressure sensitive web or, as an alternative, the pressure sensitive material may be applied to the undersurface of the stock or to the upper surface of the release liner, the release liner and stock thereafter being married. Suitable materials for base label 110 include 2.3 mil white biaxially oriented polypropylene face stock with B-122 adhesive (corresponding to adhesive 104) and a 50 pound release liner (corresponding to release liner 102), available from Brownbridge Industries, Inc. of Troy, Ohio. Suitable media 118 such as brand names, bar codes, warnings, and lot and expiration data are printed on the upper surface of base label 110. Preferably, base label 110 also has a coating of alcohol resistant varnish on the upper surface thereof to resist duration by abrasion and chemical exposure. Tab 116 is provided extending from an edge of base label 110 and underlying pull tab 136 of hanger 130. Notably, because the hanger and foot portions do not cover the entire surface of the base label, users of the label may apply further indicia. For example, a product manufacturer may wish to print suitable data adjacent the "LOT:" and "EXP." indicia. The upper surface of the base label adjacent these indicia is preferably formed from or coated with a suitable material for facilitating printing, such materials being well known in the art.

The upper surface of base label 110 is divided into adhesive zone 112 and non-adhesive zone 114 by imaginary line A. Interior area 117 of the upper surface of base label 110 is defined between legs 132A and 132B and above line A. A further vanish layer 120 is disposed on the upper surface of base label 110 throughout adhesive zone 112 except in the areas underlying foot portions 140A, 140B. To the extent that there is misregistry between the locations of varnish coating 120, the border between adhesive zone 112 and non-adhesive zone 114, and foot portions 140A, 140B, varnish coating 120 preferably overlaps into those other areas. Varnish 120 is a release varnish which allows adhesive to be removed from the upper surface of base label 110. Suitable varnishes include Paragon L075 varnish, available from Paragon Ink of Connecticut. The significance of zones 112 and 114 and varnish 120 will be discussed hereinafter. Varnish 120 may also be present underneath the portions of foot portions 140A, 140B extending between the bottoms of cutouts 144 and line A. If so, it may be desirable to apply adhesive deadener to the adhesive at these portions so that the adhesive will not interfere will handling when the hanger is in the hanging position, thus exposing the adhesive.

Hanger 130 and integrally formed foot portions 140A, 140B are constructed as follows. Hanger 130 is formed of superimposed layers 150 and 155 which are permanently secured to one another by adhesive 154. Layer 150 is formed of a relatively tear resistant, high strength material as compared to layer 155. Layer 155 is formed of a relatively stretch resistant material as compared to layer 150. The positions of layers 150 and 155 may be reversed, however, the order as described and shown is preferred.

Preferably, each of layers 150 and 155 are transparent. Layer 155 is preferably a polyester film having a thickness of from about 2 to 6 mil, and more preferably from about 3 to 4 mil. Suitable polyester films are available from Fasson of Painesville, Ohio. Layer 150 is preferably a high density polyethylene film having a thickness of from about 2 to 5 mil, and more preferably no greater than 2.5 mil (as discussed in more detail below). More preferably, layer 150 is an oriented and cross-lamination high density polyethylene film having such thickness. Suitable oriented and cross-laminated high density polyethylene films for layer 150 include VALERON™ film available from Van Leer Films. Suitable adhesives for adhesive 154 include S-3000 available from Fasson.

As noted above, layers 150 and 155 are preferably transparent. If layer 150 is formed of high density polyethylene, it has been found that the material may be rendered substantially transparent by selectively heating and stretching (simultaneously in both the machine and transverse directions) an originally cross laminated film of a prescribed thickness to a thickness of about 2.5 mil or less. It has been found that films processed in this manner but having a final thickness of greater than about 2.5 mil are not substantially transparent. Further, it has been found that two or more stacked film layers processed in this manner and each having a thickness of about 2.5 mil or less, but having a combined thickness of greater than 2.5 mil, also do not provide a substantially transparent construction. Accordingly, if layer 150 is a high density polyethylene film, layer 150 should be no greater than about 2.5 mil thick and should be formed of a unitary layer. Transparent polyester films are commonly available in a wide range of thicknesses.

Preferably, layers 150 and 155 are of the same size and shape with their respective peripheries in registry as shown, however, the layers may be differently configured. Preferably, adhesive 154 completely coats the opposed surfaces of layers 150, 155. Thus, change 130 is dual ply throughout. With reference to FIG. 2, hanger 130 includes legs 132A and 132B which terminate in ends 134A and 134B, respectively. Ends 134A and 134B are integral with, and preferably unitarily formed with, foot portions 140A and 140B, respectively.

The preferred dimensions of layers 150, 155 will depend upon the particular application and the desired appearance of the hanger. For a label 100 to be used with a conventional 250 ml IV bottle (approximate full weight 1.2 lbs.), each leg 132A, 132B should have a nominal width W of from about ⅜ inch to ½ inch, polyester layer 155 should be about 3 to 4 mil thick, and high density polyethylene layer 150 should be about 2.5 mil thick.

Foot portions 140A and 140B are substantially permanently adhered to the upper surface of base label 110 by anchoring adhesive patches 142A and 142B which coat portions of the undersurface of layer 150. Adhesive patches 142A and 142B extend up to border line A. Varnish coating 120 is present in the gap 115 between foot portions 140A and 140B. Notably, gap 115 lies adjacent interior area 117. Stress relief cutouts 144 are formed in each of foot portions 140A and 140B through each of layers 150 and 155. Film material may be provided within cutouts 144 as well, in which case the stress relief curves will be formed by cut lines in the foot portions. Pull tab 136 extends upwardly from hanger 130 and is integrally formed with, and preferably unitarily formed with, hanger 130.

Hanger 130 (including all of its layers 150, 154, 155) is transitioned from the stored position of FIG. 1 to the hanging position of FIG. 2 by grabbing pull tab 136 and lifting hanger 130 up and away from base label 110. Legs 132A and 132B fold about ends 134A and 134B, respectively. The distance between the ends of the legs is preferably chosen such that ends will be disposed diametrically opposite one another when the label is affixed to a container of a prescribed circumference. Stress relief cutouts 144 serve to inhibit the material of foot portions 140A, 140B from tearing.

As noted above layer 150 is more tear resistant than layer 155 and layer 155 is more stretch resistant than layer 150. For example, the tensile strength of a 3 mil polyester film is about 24,000–30,000 psi as compared to 8,500 psi for a 2.5 mil VALERON™ film. The tear resistance of the 2.5 mil VALERON™ film is at least 10 times as great as the tear resistance of the 3 mil polyester film (as measured in terms of unit grams force required to propagate a tear). Hanger 130 having both of superimposed layers 150, 155 with their respective different properties provides all of the benefits of a film hanger while insuring against catastrophic failure of the hanger. Layer 155 provides break strength and stretch resistance so that the hanger does not stretch under a prescribed load. Layer 150 provides tear resistance. Thus, while the material of layer 155 has a tendency to tear if nicks or the like are present, such tears are prevented from propagating by the tear resistance of layer 150. On the other hand, while layer 150 has a tendency to stretch under load, particularly over long periods of time, stretching of the hanger is prevented by layer 155. Hanger may be diecut from a composite web as described below, thereby allowing for efficient and cost-effective manufacture using conventional methods and apparatus. Moreover, because each of films 150, 155 and adhesive 154 are transparent materials, indicia 118 is visible through the hanger both to an observer and to an electronic bar code reader.

Figure 4:
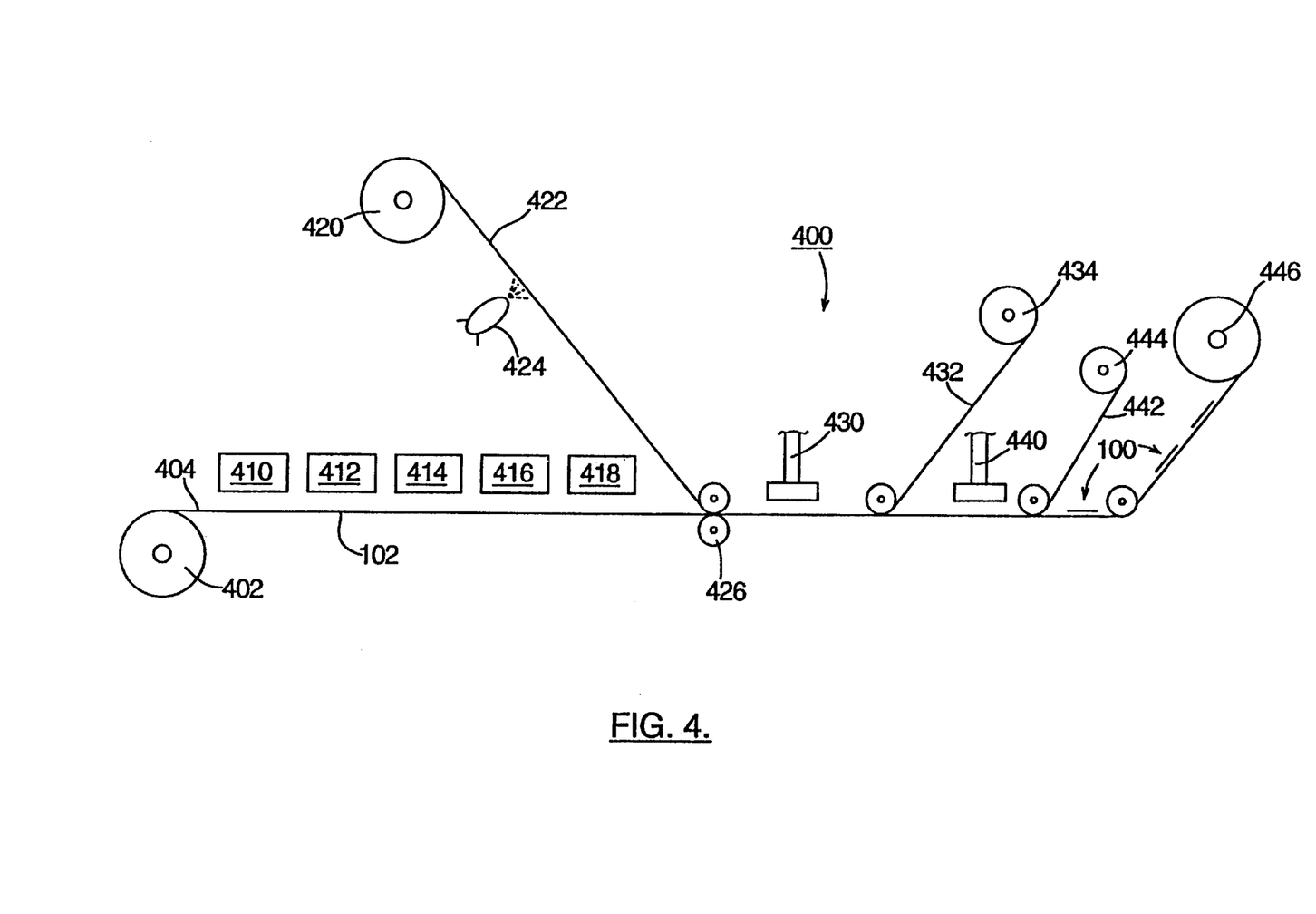
FIG. 4 is a schematic diagram showing an apparatus for forming labels of the present invention according to a first method using a pre-formed multi-ply web for forming the hangers.

With reference to FIG. 4, an apparatus for forming labels 100 according to the first embodiment is shown schematically therein. Apparatus 400 may include, for example, a Mark Andy 2200 Flexopress available from Mark Andy, Inc. of Chesterfield, Mo. Alternatively, rotary letter press, lithographic printing, silk screen, or gravure may be used.

First, a web of pressure sensitive film or paper 404 is unwound from unwind station 402. Preferably, web 404 includes a release liner and a stock web adhered thereto by a pressure sensitive adhesive. Alternatively, base web 404 may be formed by applying adhesive to the underside of a stock web on line prior to marrying the stock web to the release liner. The stock material and pressure sensitive adhesive correspond to base label 110 and adhesive 104 of the finished labels 100. Web 404 is passed through one or more print stations 410 at which indicia 118 is applied to the upper surface of the web. Alcohol resistant varnish is applied at varnish station 412 and cured at curing station 414. Release varnish 120 is applied at varnish station 416 and cured at curing station 418. More particularly, varnish applying station 416 applies varnish in the areas of base web 404 corresponding to non-adhesive zone 112 in a pattern excluding the portions corresponding to feet 140A and 140B.

A pre-formed composite web 422 is unwound from unwind station 420. Web 422 corresponds to hanger 130 and foot portions 140A, 140B of label 100. Web 422 is formed of (1) an upper continuous web of polyester or other suitable material as described above for layer 155 of hanger 130 and (2) a lower continuous web of VALERON™ or other suitable material as described above for layer 150, secured together by (3) a layer of adhesive therebetween corresponding to adhesive 154.

Adhesive applicator 424 applies adhesive to the underside of web 422. Adhesive applicator 424 is preferably a screen coater as available from Nordson Corporation of Alpharetta, Ga. Adhesive applicator 424 forms a continuous, longitudinal band on the underside of web 422 corresponding to adhesive zone 112 of label 100. That is, adhesive applicator 424 forms a band of adhesive along one side edge of the web 422 while leaving a non-adhesive band adjacent the other side of the web.

Webs 422 and 404 are married at nip rollers 426. The adhesive applied by adhesive applicator 424 serves to adhere the lower portion of web 422 to the upper surface of web 404. More particularly, the portions of web 422 corresponding to foot portions 140A and 140B are permanently secured to the non-release varnish coated portions of base web 404. The remainder of the adhesive on the underside of web 422 is releasably secured to the release varnish coated portions of base web 404.

Thereafter, due cutter 430 forms cut lines in web 422 through each of the lower and upper webs and adhesive (corresponding to layers 150, 155 and adhesive 154) down to base web 404 to define hanger 130 and foot portions 140A, 140B. Upper waste matrix 432 consisting of the portions of web 422 and the adhesive thereon not lying within hanger 130 and foot portions 140A, 140B is pulled away by winding station 434. Release varnish 130 allows the adhesive on the undersurface of web 422 to be released from base web 404 and removed with the waste matrix. Notably, release varnish coated gap 115 connects the continuous portion of the waste matrix below the foot portions to the portion of the waste matrix defined between legs 140A and 140B (i.e., overlying interior area 117). In this way, the entire waste matrix of web 422 outside of hanger 130 and foot portions 140A, 140B may be removed as a continuous piece, thereby allowing continuous removal.

Thereafter, base labels 110 are formed by die cutter 440 which forms die cuts through base web 404 down to release liner 102. The waste matrix 442 of base web 404 is removed by winding station 444. The resulting labels 100 disposed on release liner 102 may thereafter be wound onto winding station 446 or sheeted and stacked.

In some cases, it may be feasible to dispense with the use of the release varnish. This may be possible in cases where the adhesive is not allowed sufficient time to set, and can therefore be stripped away before it becomes permanently adhered to the base web.

Figure 5:
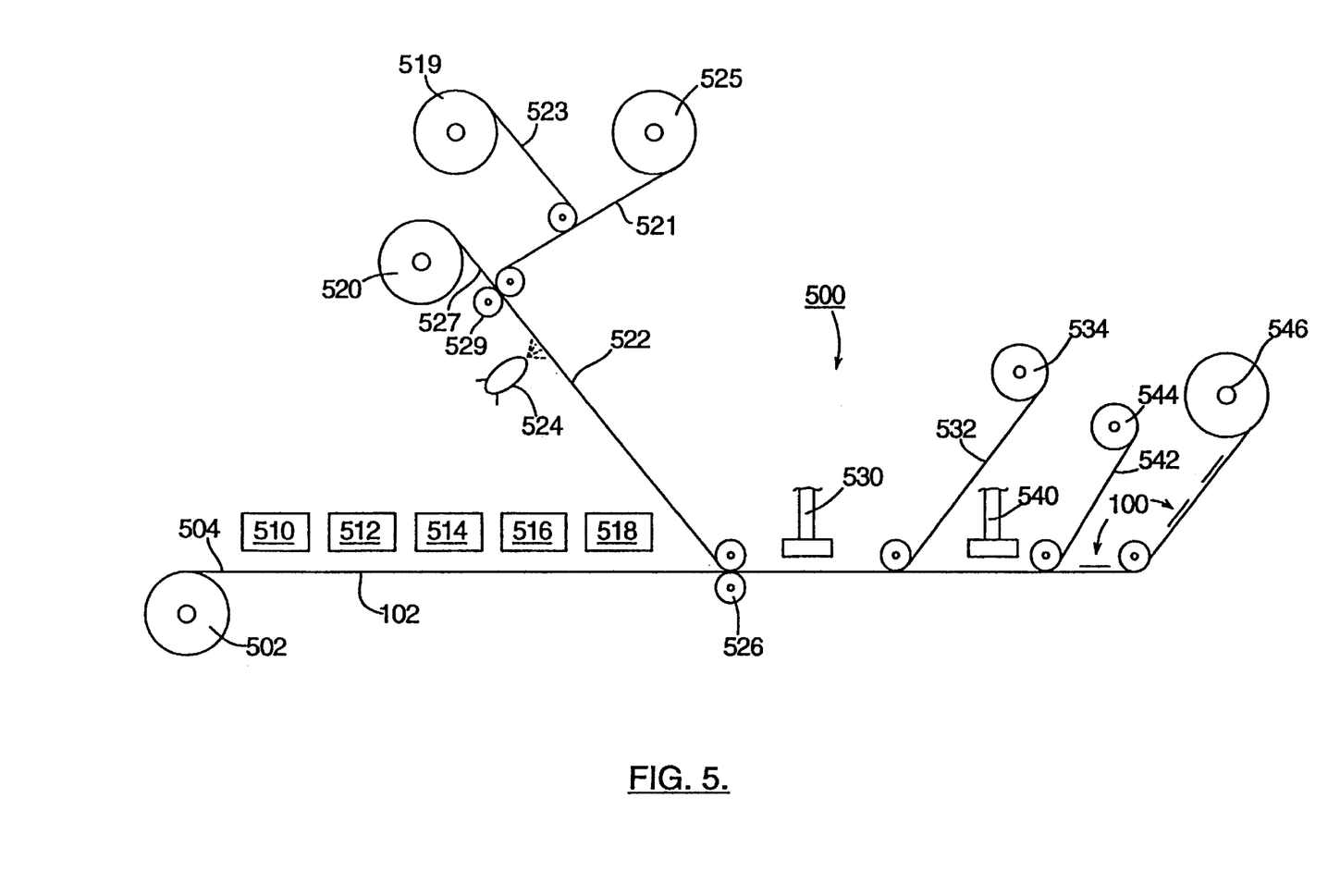
FIG. 5 is a schematic diagram of an apparatus for forming labels of the present invention according to a second method using two separate webs for forming the hangers.

With reference to FIG. 5, an apparatus 500 for forming labels 100 according to a second method is shown therein. Elements 502, 504, 510, 512, 514, 516, 518, 524, 526, 530, 532, 534, 540, 542, 544, and 546 correspond to elements 402, 404, 410, 412, 414, 416, 418, 424, 426, 430, 432, 434, 440, 442, 444, and 446 of apparatus 400. Web 522 corresponds to web 422 but differs in that it is formed in-line on the apparatus rather than being performed. Namely, web 527 corresponding to layer 150 is unwound from unwind stand 520. Web 521 corresponding to layer 155 and adhesive 154 is unwound from unwind stand 525. With 521 is preferably pre-coated with pressure sensitive adhesive on its lower surface, the adhesive covered with a release liner 523 (removed by unwind stand 519), however, adhesive may be applied by an adhesive applicator (not shown) after unwinding and prior to marrying of webs 521 and 527 by nip rollers 529. The operation of apparatus 500 is otherwise as described above with regard to apparatus 400.

Each of the labels are described above may be produced "multiple up" on a web. That is, a plurality of labels may formed across a relatively wide web which may thereafter be slit into individual webs.

Either the upper surfaces or the lower surfaces of each of the layers of the hangers may be printed on. As noted above, each layer of the hanger material is preferably transparent. In this way, if the hanger is not printed, the base label may be printed without regard for the placement of the hanger in either of the stored or operative positions.

From the foregoing, it will be appreciated by those of ordinary skill in the art that labels 100 may be constructed according to other methods. Moreover, the labels may be modified in various ways while still employing a multi-ply hanger as described. For example, a hanger according to the present invention may be used and incorporated in various labels and methods as described in applicants' U.S. patent application Ser. No. 08/647,466, filed May 3, 1996, the disclosure of which is incorporated herein in its entirety. The means and methods for such use and incorporation will be apparent to those of ordinary skill in the art upon a reading of said patent application disclosure and the description hereinabove. Among the possible modifications to the labels and methods contemplated, adhesive may be applied to the base web rather than the hanger web. Hangers 130 may be preformed and applied by hand or by machine to a base web corresponding to base 110, adhesive being applied to either of the hangers or the base web. Rather than employing varnish 120, the adhesive patches which secure the foot portions to the base may be applied using a suitable adhesive applicator such as a slot coater or screen printer. Rather than applying adhesive only to the hanger web or the base web at locations corresponding to the foot portions, the entire underside of the hanger web may be coated with adhesive and portions of the adhesive outside of the foot portions in turn coated with an adhesive deadener.

Figures 6, 7:
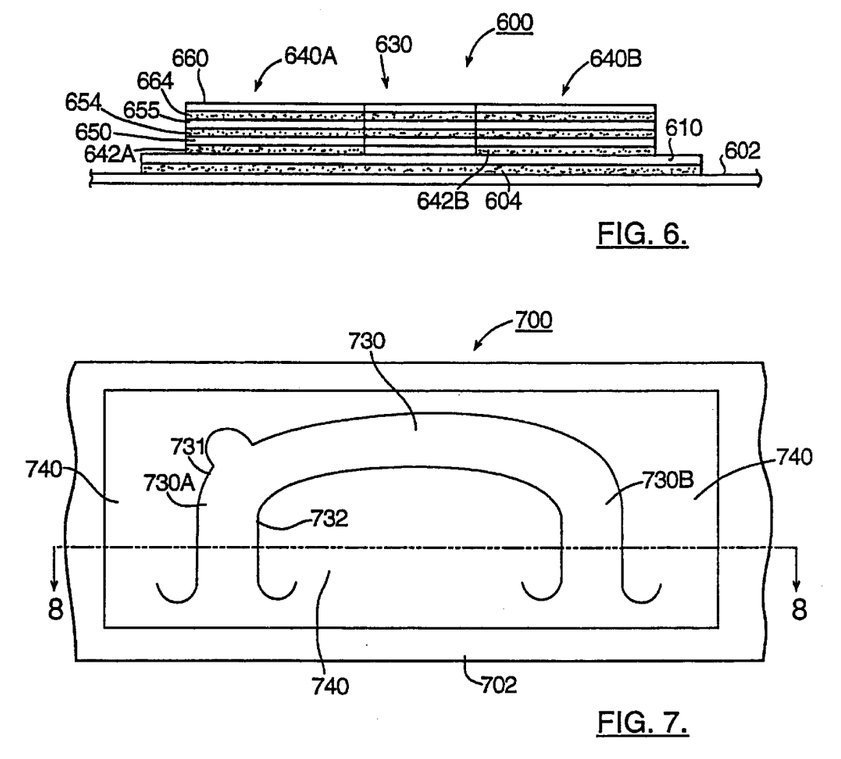
FIG. 6 is a side elevational view of a label incorporating a change according to a second embodiment disposed on a release liner.
FIG. 7 is a top plan view of a label according to a third embodiment of the present invention.

With reference to FIG. 6, a label 600 according to a second embodiment of the present invention is shown therein. Label 600 includes hanger 630 corresponding to hanger 130 of the first embodiment except as follows. Hanger 630 includes layer 650 corresponding to layer 150 preferably formed of transparent linear low density polyethylene. Layer 650 is secured to layer 655 by adhesive 654 corresponding to adhesive 154. Layer 655 is formed of the same material as described with respect to layer 155. Layer 660 is secured to the upper surface of layer 655 by adhesive 664, preferably the same type adhesive as used for layer 154. Layer 660 is preferably formed of the same material as layer 650. It will be appreciated that hanger 630 being so constructed provides the same advantages as described above with regard to hanger 130. Additionally, the provision of tear resistant layers 650 and 600 on either side of stretch resistant layer 655 serves to shield stretch resistance layer 655 from nicks and cuts both when the hanger is in the stored position and when the use. Elements 602, 604, 610, 640A, 640B, 642A, and 642B correspond to elements 102, 104, 110, 140A, 140B, 142A, and 142B of label 100, respectively.

Figure 8:
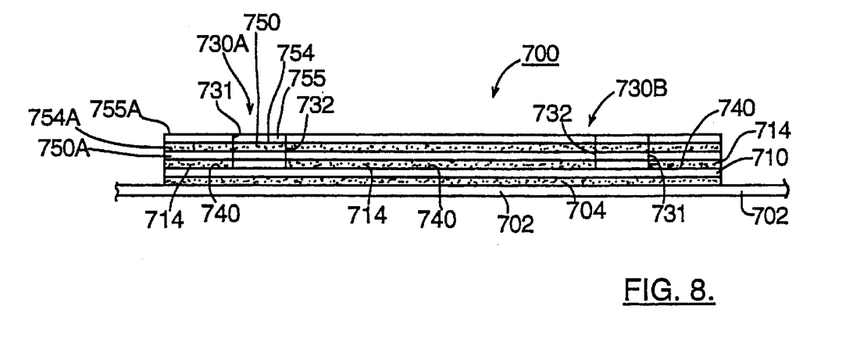
FIG. 8 is a side, cross-sectional view of the label of FIG. 7 taken along the line 8—8.

With reference to FIGS. 7 and 8, a label 700 according to a third embodiment is shown therein. Label 700 is disposed on release liner 702 and includes pressure sensitive adhesive 704 and base layer 710 corresponding to elements 104 and 110 of label 100. Label 700 further includes pressure sensitive adhesive 714, layer 750A, pressure sensitive adhesive 754A, and layer 755A. Layer 750A is preferably formed from the same materials and has the same characteristics as described above with respect to layer 150 of the first embodiment. Layer 755A is preferably formed from the same materials and has the same characteristics as layer 155 of label 100. Hanger 730 having legs 730A and 730B is defined in layers 750A, 754A, and 755A by cut lines 731 and 732 which extend through each of the layers. More particularly, hanger 730 has elements 750, 754, and 755 formed from layers 750a, 754a, and 755a, respectively, and corresponding to elements 150, 154, and 155 of label 100, respectively. Adhesive layer 714 is interposed between and secures base layer 710 to layers 750A at areas 750 throughout label 700 except at the portions underlying hanger 730.

From the foregoing, it will be appreciated that hanger 730 may be pulled up and away from base layer 710 and will be secured by the ends of its legs to the base label and an associated article to which the base label is secured by adhesive 704. Hanger 730 so constructed provides the advantages attributable to the composite construction and the selected performance characteristics as discussed above with regard to hanger 130. Means and methods for manufacturing labels 700 will be readily apparent to those of ordinary skill in the art upon a reading of the foregoing description and the disclosure of U.S. Pat. No. 5,135,125 to Andel, et al., the disclosure of which is hereby incorporated in its entirety by reference.

EXAMPLE 1

A label according to the present invention having the following construction was tested as described below. Each leg of the hanger had a nominal width of ⅜ inch and layers 150, 155 were identically shaped and aligned.

| Component | Material |
|---|---|
| release liner 102 | 50 lb. Kraft liner |
| adhesive 104 | Brownbridge B-122 adhesive |
| base label 110 | Brownbridge 2.3 mil biaxially oriented polypropylene with an imprintable clay top coating |
| adhesive 142A, 142B | Fasson S-3000 adhesive |
| layer 155 | clear 3 mil polyester film |
| adhesive 154 | Fasson S-3000 adhesive |
| layer 150 | 2.5 mil BTX Valeron (heated and stretched as described above to make the film transparent) |

The label was secured to a bottle weighing approximately 1.2 lbs. (conventional IV 250 ml bottle, filled with fluid) and suspended from a hook. A 10 lb. weight was attached to the bottle. The bottle remained suspended for 100 hours without breakage or stretching of the label in excess of ½ inch. A label as described above was also suspended on an Ametek ACCUFORCE II model no. M-L 4433 tensile strength tester. The measured tensile strength was between 40 to 50 lbs. and the hanger material stretched about ½ inch. The overall hanger was substantially transparent.

EXAMPLE 2

A label having components corresponding to elements 102, 104, 110, adhesive 142A, 142B, and layer 150 was constructed as described for the first example except that layer 150 was a 5 mil polyester film and adhesive 154 and layer 155 was omitted. The tensile strength of this label, as measured by the Ametek pull tester, was approximately 35 lbs. and the hanger material stretched about ½ inch. No nicks or cuts were introduced to the polyester film as may occur in normal usage.

EXAMPLE 3

A label having components corresponding to elements 102, 104, 110, adhesive 142A, 142B, and layer 150 was constructed as described for the first example except that layer 150 was an 8.6 mil Valeron film and adhesive 154 and layer 155 were omitted. The tensile strength of this label, as measured by the Ametek pull tester, was approximately 54 lbs. and the hanger material stretched about 8 to 12 inches. The Valeron film layer was substantially opaque.

White it is generally preferred that the film hanger be constructed from at least one relatively stretch resistant, high break strength film and at least one layer of tear resistant film, it is also contemplated that a multi-ply hanger may be formed using only layers of stretch resistant, high break strength material. For example, with reference to FIG. 1, layer 150 rather than being formed of a tear resistant material such as VALERON™ may be formed from the same or a similar material to that as described for layer 155, for example, polyester film. The composite hanger so formed may comprise further superimposed layers as well. Notably, the hanger will only tear if a nick or cut is formed in all of the superimposed layers 150, 155 at substantially the same location. Thus, the chances of catastrophic failure of the hanger are substantially reduced. In particular, for the same film materials, the tear propagation rate for the multi-ply hanger is substantially less than that for a single layer hanger having a thickness the same as the sum of the thickness of multiple layers. Further, the presence of adhesive between the adjacent layers 150, 155 serves to diffuse the stresses which otherwise concentrate to accelerate tear propagation. Preferably, in this embodiment, layers 150 and 155 are identical.

As a further alternative, layer 150 may be a high density polyethylene film as described above with layer 155 being a low density polyethylene film instead of polyester. Alternatively, layer 150 may be a high density polyethylene with layer 155 being an oriented polypropylene.

Figure 9:
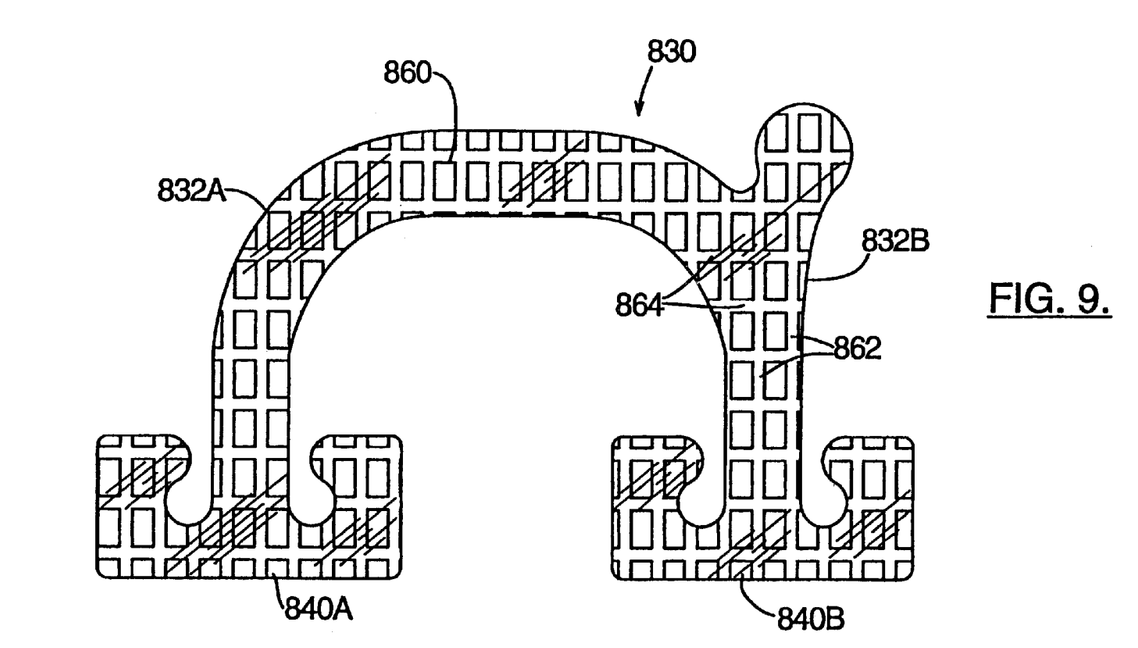
FIG. 9 is a top plan view of hanger according to a fourth embodiment of the present invention incorporating a scrim.
Figure 10:
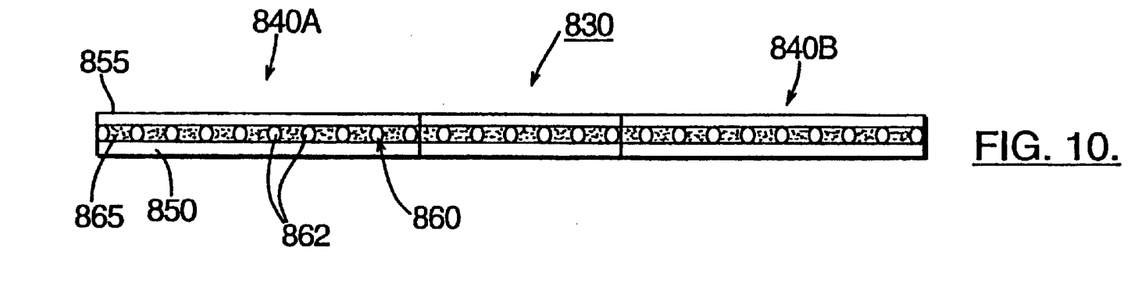
FIG. 10 is a side elevational view of the hanger of FIG. 9.

With reference to FIGS. 9 and 10, a hanger 830 according to a fourth embodiment is shown therein. It will be readily appreciated from the description which follows that hanger 830 may be used in place of and in the same manner as hangers 130, 630, and 730 of the labels of the preceding embodiments. Hanger 830 has legs 832A, 832B with respective foot portions 840A, 840B. Hanger 830 is characterized in that it includes scrim 860 sandwiched between layers 850 and 855. Layers 850, 855 and scrim 860 are permanently adhered to one another by adhesive 865 as shown in FIG. 10.

Scrim 860 may be any suitable scrim or mesh material. Preferably, scrim 86 is formed from woven polyester warp strands 864 and weft strands 862. Suitable scrim material includes STABILLON™ polyester or glass filament scrim available from the Milliken Specialty Industrial Division. The strand density in both the warp and weft directions is preferably about 3 to 4 strands per inch with a strand thickness of from about 520 to 560 microns. The strands are preferably transparent.

Film layers 850 and 855 may be chosen to provide additional tensile strength and/or tear resistance to the hanger or may be chosen without regard to performance characteristics. For example, suitable materials would include linear low density polyethylene or low thickness high density polyethylene if it were desired to provide additional tear resistance. Preferably, film layers 850 and 855 are each transparent Adhesive 865 is preferably Fasson S-3000.

Because, as shown, each of layers 850 and 855 is transparent, the overall hanger 830 is substantially transparent. Thus, the hanger incorporating the scrim will provide the same benefits as described above attributable to a transparent hanger, namely, that any underlying indicia on the base label will be visible therethrough. Moreover, the construction of the scrim provides an inherent improved tear resistance. Because the scrim is formed of individual strands the tear propagation mechanism of a film is not present.

Labels incorporating hangers 830 may be formed in substantially the same manner as labels 100. However, pre-formed composite web 422 is replaced with a pre-formed composite web consisting of a continuous web corresponding to layer 850, a continuous web corresponding to layer 855, a continuous band of scrim corresponding to scrim 860, and a continuous layer of adhesive corresponding to adhesive 865. The pre-formed composite web may be constructed by supplying the webs corresponding to layers 850 and 855 as self-adhesive webs. The self adhesive webs are placed on a web press and drawn through a nip roller with the band of scrim therebetween and their self adhesive surfaces facing one another and respective opposed sides of the scrim. Alternatively, the supplied web corresponding to webs 850, 855 may be non-self adhesive with adhesive being applied to one or both webs prior to lamination of the webs and the scrim.

In addition to or in place of adhesive, the layers of the hanger may be secured to one another by mechanical adhesion (i.e., heat the films and run them together under pressure through a nip roller) or a suitable welding process.

In each of the above described hangers and labels it may be desirable to provide means for verifying that a hanger is mounted on each label. In the hanger embodiments wherein the layers of the hanger are secured to one another by adhesive (e.g., adhesive layer 154), the adhesive may include a photo-luminescent additive. Suitable adhesives of this type include Fasson PL-3000. If the layers are mechanically adhered or welded together, a photo-luminescent material may be printed on one or more of the hanger layers. A conventional sensor may be used to detect the presence of the photo-luminescent material and thereby the hanger.

While a preferred embodiment of the present invention has been described, it will be appreciated by those of skill in the art that certain modifications may be made without departing from the scope of the present invention. All such modifications are intended to come within the scope of claims which follow.

What is claimed is:

1. A hanger having at least two interconnected legs defining an opening therebetween, each of said legs having a respective end, said hanger including at least first and second superimposed polymeric film layers, wherein said first layer has a tensile strength greater than said second layer and said second layer has a tear resistance greater than said first layer.

2. The hanger of claim 1 wherein each of said first and second layers is substantially transparent.

3. The hanger of claim 1 wherein said first layer is formed of polyester.

4. The hanger of claim 1 wherein said second layer is formed of high density polyethylene.

5. The hanger of claim 4 wherein each of said first and second layers is substantially transparent.

6. The hanger of claim 1 wherein said first layer is formed of polyester and said second layer is formed of high density polyethylene.

7. The hanger of claim 1 wherein said first and second layers are secured to one another by mechanical adhesion.

8. The hanger of claim 1 wherein said first and second layers are secured to one another by welding.

9. The hanger of claim 1 wherein at least one of said first and second layers is printed with a photo-luminescent material.

10. The hanger of claim 1 wherein said first and second layers are secured to one another by a layer of hanger adhesive interposed therebetween.

11. The hanger of claim 10 wherein said hanger adhesive includes a photo-luminescent material.

12. The hanger of claim 10 wherein said first layer, said second layer, and said layer of hanger adhesive are substantially coextensive.

13. The hanger of claim 1 wherein said hanger includes at least three superimposed polymeric film layers.

14. The hanger of claim 1 wherein each of said first and second superimposed polymeric film layers are formed of polyester film.

15. A hanger having at least two interconnected legs defining an opening therebetween, each of said legs having a respective end, said hanger including a scrim and a backing layer secured to said scrim.

16. The hanger of claim 15 wherein said backing layer is a polymeric film.

17. The hanger of claim 16 wherein said backing layer is transparent.

18. The hanger of claim 17 wherein said scrim is transparent.

19. The hanger of claim 15 including a second backing layer secured to said scrim, wherein said first and second backing layers are disposed on opposed surfaces of said scrim.

20. The hanger of claim 19 wherein each of said first and second backing layer is transparent.

21. The hanger of claim 15 wherein said backing layer is secured to said scrim by adhesive.

22. The hanger of claim 21 wherein said adhesive includes a photo-luminescent material.

* * * * *